(12) United States Patent
Bhongale et al.

(10) Patent No.: US 10,996,367 B2
(45) Date of Patent: May 4, 2021

(54) CHEMICAL SENSING USING MAGNETIC COMPLEXES

(71) Applicant: Halliburton Energy Services, Inc., Houston, TX (US)

(72) Inventors: Satyan Gopal Bhongale, Cypress, TX (US); Li Gao, Katy, TX (US); Daniel Joshua Stark, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/343,860

(22) PCT Filed: Dec. 12, 2016

(86) PCT No.: PCT/US2016/066197
§ 371 (c)(1),
(2) Date: Apr. 22, 2019

(87) PCT Pub. No.: WO2018/111222
PCT Pub. Date: Jun. 21, 2018

(65) Prior Publication Data
US 2020/0142091 A1  May 7, 2020

(51) Int. Cl.
| | | |
|---|---|---|
| *G01V 3/28* | (2006.01) | |
| *G01N 33/38* | (2006.01) | |
| *E21B 47/10* | (2012.01) | |
| *E21B 49/00* | (2006.01) | |
| *E21B 47/005* | (2012.01) | |

(Continued)

(52) U.S. Cl.
CPC ............ *G01V 3/28* (2013.01); *E21B 47/005* (2020.05); *E21B 47/10* (2013.01); *E21B 49/00* (2013.01); *G01N 33/383* (2013.01); *E21B 33/14* (2013.01); *E21B 43/16* (2013.01); *E21B 43/26* (2013.01)

(58) Field of Classification Search
CPC ......... G01V 3/28; E21B 47/005; E21B 47/10; E21B 43/26; E21B 33/14; E21B 43/16; E21B 49/00; G01N 33/383
See application file for complete search history.

(56) References Cited

U.S. PATENT DOCUMENTS

| | | |
|---|---|---|
| 6,502,634 B1 | 1/2003 | Evans et al. |
| 7,712,527 B2 | 5/2010 | Roddy |

(Continued)

FOREIGN PATENT DOCUMENTS

WO   2011017415   2/2011

OTHER PUBLICATIONS

ISRWO International Search Report and Written Opinion for PCT/US2016/066197 dated Aug. 18, 2017.

(Continued)

*Primary Examiner* — Akm Zakaria
(74) *Attorney, Agent, or Firm* — Thomas Rooney; C.Tumey Law Group PLLC (57) ABSTRACT

Disclosed herein are methods and systems that use magnetic complexes in wellbore monitoring. A well monitoring system may comprise magnetic complexes disposed in a subterranean formation, wherein the magnetic complexes each comprise a first magnetic portion, a second magnetic portion, and a spacer portion; and an electromagnetic interrogator, wherein the electromagnetic interrogator comprises an electromagnetic source and an electromagnetic detector.

20 Claims, 5 Drawing Sheets

(51) Int. Cl.
*E21B 43/26* (2006.01)
*E21B 33/14* (2006.01)
*E21B 43/16* (2006.01)

(56) References Cited

U.S. PATENT DOCUMENTS

| | | | |
|---|---|---|---|
| 8,456,166 B2* | 6/2013 | DePavia | G01V 3/28 |
| | | | 324/333 |
| 8,471,559 B2 | 6/2013 | Taherian et al. | |
| 8,692,547 B2 | 4/2014 | Chem et al. | |
| 9,084,820 B2 | 7/2015 | Zabow et al. | |
| 10,287,877 B2* | 5/2019 | Gianchandani | E21B 43/267 |
| 2002/0179301 A1 | 12/2002 | Schultz et al. | |
| 2002/0195247 A1* | 12/2002 | Ciglenec | E21B 47/12 |
| | | | 166/250.11 |
| 2004/0090230 A1* | 5/2004 | Appel | G01V 3/32 |
| | | | 324/307 |
| 2008/0007253 A1* | 1/2008 | Takahata | G01D 5/2066 |
| | | | 324/207.22 |
| 2011/0192597 A1 | 8/2011 | Roddy et al. | |
| 2011/0198078 A1* | 8/2011 | Harrigan | E21B 49/087 |
| | | | 166/254.2 |
| 2012/0253680 A1* | 10/2012 | Thompson | E21B 41/0092 |
| | | | 702/13 |
| 2013/0307564 A1* | 11/2013 | Colosimo | G01N 27/221 |
| | | | 324/647 |
| 2014/0262234 A1 | 9/2014 | Walton et al. | |
| 2017/0204721 A1* | 7/2017 | Babakhani | E21B 47/13 |
| 2017/0227666 A1* | 8/2017 | Legendre | G01V 3/20 |

OTHER PUBLICATIONS

Webb, A.G., Dielectric Materials in Magnetic Resonance, Concepts Magn. Reson., 38A: 148-184. (2011).
Lutz Trahms, Martin Burghoff, NMR at very low fields, Magnetic Resonance Imaging, vol. 28, Issue 8, Oct. 2010.
Evan Mah and Raja Ghosh, Thermo-Responsive Hydrogels for Stimuli-Responsive Membranes, Processes 2013, 1, 238-262.
Ick Chan Kwon, You Han Bae & Sung Wan Kim, Electrically erodible polymer gel for controlled release of drugs, Nature, 354(6351), 291-293, 1991.
Liang-Yin Chu, et al., Thermoresponsive Transport Through Porous Membranes with Grafted PNIPAM Gates, AIChE Journal, 2003.
G. Zabow, SIJ. Dodd & A.P. Koretsky, Shape-Changing Magnetic Assemblies as High-Sensitvity NMR-Readable Nanoprobes, Letter, 2015.

* cited by examiner

CHEMICAL SENSING USING MAGNETIC COMPLEXES

BACKGROUND

Natural resources such as gas, oil, and water residing in a subterranean formation or zone may be recovered by drilling a wellbore into the subterranean formation while circulating a drilling fluid in the wellbore. After terminating the circulation of the drilling fluid, a string of pipe (e.g., casing) may be run in the wellbore. The drilling fluid may then be circulated downward through the interior of the pipe and upward through the annulus, which is located between the exterior of the pipe and the walls of the wellbore. Next, primary cementing may be performed whereby a cement slurry is placed in the annulus and permitted to set into a hard mass (i.e., sheath) to thereby attach the string of pipe to the walls of the wellbore and seal the annulus. The pipe may be perforated at certain points to allow the natural resources to flow from the formation into the well. If desired, the surrounding subterranean formation may be fractured to increase permeability and enhance flow from the formation. Secondary recovery techniques may also be used to increase production. An example of a secondary recovery technique may include water flooding in which water may be injected into a subterranean formation by way of a water injection well to displace hydrocarbons to a producing well.

At different periods in the life of the well, it may be desirable to monitor various parameters in situ. By way of example, it may be desirable to monitor flow of water in a water flood operation from the water injection well to the producing well. In cementing, it may be desirable to monitor cement curing, for example, to determine cement set time and reduce wait-on-cement time. Well cementing may also be monitored, for example, to determine the interface between the cement and other well fluids, such as the spacer fluid. In fracturing, it may also be desirable to map fracture dimensions. In situ monitoring may be performed by use of active, embedded sensors placed downhole. However, such embedded sensors can involve drawbacks that make them undesirable for use in a wellbore environment. For example, low-powered (e.g., nanowatt) electronic moisture sensors are available, but have inherent limitations when used downhole. For example, the highly alkali environment in well cement can damage their electronics, and they may be sensitive to electromagnetic noise. Additionally, power must be provided from an internal battery to activate the sensor and transmit data, which increases sensor size and decreases useful life of the sensor.

BRIEF DESCRIPTION OF THE DRAWINGS

These drawings illustrate certain aspects of some of the embodiments of the present invention, and should not be used to limit or define the invention.

DETAILED DESCRIPTION

Disclosed herein are methods and systems that use magnetic complexes in wellbore monitoring. More particularly, the methods and systems may detect chemicals remotely by measuring the response of the magnetic complexes by application of an electromagnetic field. The magnetic complexes may be stimuli sensitive so that their response to the electromagnetic field may vary. By way of example, the structure and shape of the magnetic complexes may vary based on application of stimuli, thus also changing their response to the electromagnetic field. Accordingly, by measuring the response of the magnetic complexes to the electromagnetic field, a number of different downhole parameters may be monitored, such as geometry, hydration state, chemical composition, temperature, and local field strength. Advantageously, the magnetic complexes may be passive so they may be assembled without any active (e.g., powered) components. For example, the magnetic complexes may not require continuous power from a battery or external power source in order to operate.

Figure 1:
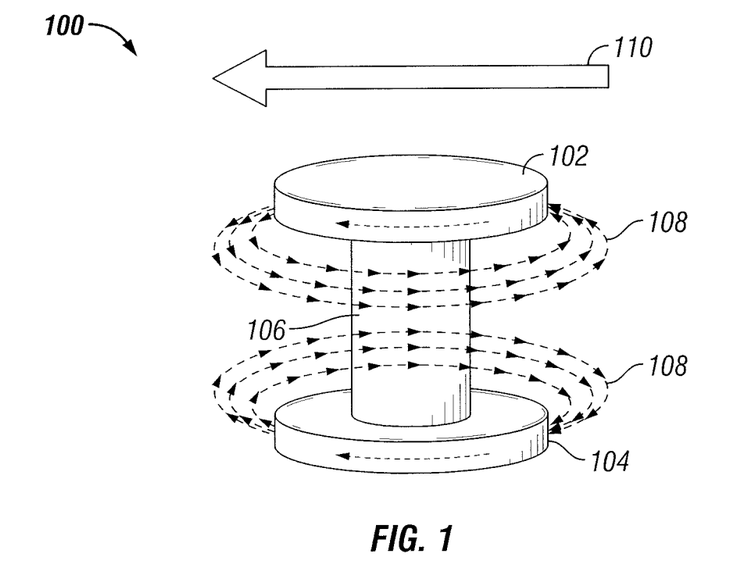
FIG. 1 is a schematic illustration of an example magnetic complex.

Referring now to FIG. 1, a schematic illustration of a magnetic complex 100 is provided. As illustrated, the magnetic complex 100 may comprise a first magnetic portion 102 and a second magnetic portion 104. The first magnetic portion 102 and the second magnetic portion 104 may be separated by a spacer portion 106. The spacer portion 106 may be coupled to the first magnetic portion 102 and the second magnetic portion 104 using any suitable technique. By way of example, the magnetic complex 100 may be microfabricated. A wide variety of suitable microfabrication techniques may be used, including those that involve evaporation of successive layers of magnetic material and photoresist with ion milling to define the first magnetic portion 102 and second magnetic portion 104 from the magnetic material. Other example microfabrication techniques may include, without limitation, lift-off patterning. The first magnetic portion 102 and the second magnetic portion 104 may be any suitable configuration. As illustrated, the first magnetic portion 102 and the second magnetic portion 104 may be disc-shaped. However, other shapes for the first magnetic portion 102 and second magnetic portion 104 may be suitable, including, without limitation, plate-shaped (e.g., rectangular, square, oval, etc.), cubic-shaped, cuboid-shaped, irregular-shaped, hemi-spherical spaced or otherwise formed.

The first magnetic portion 102 and the second magnetic portion 104 may be arranged so that, upon application of an external electromagnetic field 110, the first magnetic portion 102 and the second magnetic portion 104 may be magnetized with induced magnetic fields 108 between them as indicated in FIG. 1. The shape of the spacer portion 106 may influence the properties (e.g., strength) of the induced fields 108 between the first magnetic portion 102 and second magnetic portion 104. As will be discussed in more detail below, these induced magnetic fields 108 may be remotely monitored to determine one or more downhole parameters. Without limitation, changing in shape of the spacer portion 106 may result in a change in geometry between the first magnetic portion 102 and the second magnetic portion 104. Non-limiting examples of a geometry change may include changing in spacing between the first magnetic portion 102 and the second magnetic portion 104 and changing an angle (e.g., tilt or rotation) between first magnetic portion 102 and second magnetic portion 104. Another alternative technique that may be used for the geometry change may include increasing a radius of the spacer portion 106. By changing the geometry, the field strength of the induced electromagnetic fields 108 may change as well as the frequency response of the magnetic complex 100 comprising the first magnetic portion 102, second magnetic portion 104, and spacer portion 106. Nanoparticles may also be included in the spacer portion 106. These nanoparticles may be very small (e.g., less than 10 nanometers, such as 1-2 nanometers) or formed from a material such as gold or iron oxide so that the nanoparticles would impact the response of the magnetic complex 100. By including the nanoparticles in the spacer portion 106, different types of magnetic complexes 100 may be tagged or a different interaction mechanism, such as light, may be used.

The first magnetic portion 102 and the second magnetic portion 104 may include structures formed from magnetic and/or magnetizable materials By way of example, the first magnetic portion 102 and the second magnetic portion 104 should comprise materials that cause them to generate magnetic fields (e.g., induced magnetic fields 108) either alone or in response to external electromagnetic field 110. Without limitation, the first magnetize portion 102 and the second magnetic portion 104 may include any of a variety of magnetic and/or magnetizable materials, including ferromagnetic, ferrimagnetic, paramagnetic, superparamagnetic, antiferromagnetic materials, and combinations thereof. The first magnetic portion 102 and the second magnetic portion 104 may also include alloys or compounds of these magnetic and/or magnetizable materials. Non-limiting examples of suitable materials may include soft magnetic materials such as Fe—Si, Fe, Ni, Ni—Fe, Fe—Co, Mn—Zn ferrites, or hard ferromagnetic materials such as Co—Cr, Sm—Co, Nd—Fe—Be, Al—Ni—Co, etc. They may also consist of Group III, IV, and/or V magnetic materials, such as Q-Carbon. The first magnetic portion 102 and second magnetic portion 104 may be made from a combination of materials. The first magnetic portion 102 and second magnetic portion 104 may be made from different materials or of heterostructures, such as a ferromagnetic ring encircling a paramagnetic center. The first magnetic portion 102 and the second magnetic portion 104 may include filler materials that are non-magnetic/weakly magnetic.

Spacer portion 106 may separate the first magnetic portion 102 and the second magnetic portion 104. Without limitation, spacer portion 106 may comprise a hydrogel, water-swellable elastomers, and thermoplastic-elastomer composites, water-swellable clays, or combinations thereof. Hydrogels are generally a polymeric material in the form of a three-dimensional network of polymer chains that are capable of holding water in the three-dimensional network. Hydrogels may be homopolymer hydrogels, copolymer hydrogels, or multipolymer interpenetrating polymer hydrogels. Without limitation, the polymeric material may be nonionic, ionic, amphoteric, or zwitterionic. Without limitation, the polymeric material may comprise a natural polymer, such as collagen, gelatin, or polysaccharides (e.g., starch, alginate, and agarose), or a synthetic polymer. Non-limiting examples of polymer materials in the hydrogel may include polyacrylamide, hydrolyzed polyacrylamide, copolymers of acrylamide with ethylenically unsaturated ionic comonomers, copolymers of acrylamide and acrylic acid salts, poly(acrylic acid) or salts thereof, polyethyleneglycol, polyvinylpyrrolidone, polyvinylalcohol, carboxymethyl cellulose, hydroxyethyl cellulose, hydroxypropyl cellulose, guar gum, carboxymethyl guar, carboxymethyl hydroxypropyl guar gum, hydrophobically associating swellable emulsion polymers, and latex polymers. The polymer material may be functionalized, for example, with one or more groups grafted onto the polymer. Without limitation, the polymer material may include functional groups, such as amino, carboxyl or salts thereof, hydroxyl, thiol, acid anhydride, acid chloride, and/or isocyanate groups.

The spacer portion 106, for example, comprising the hydrogel may be stimuli responsive. Without limitation, the spacer portion 106 may be designed such that its configuration changes in response to pH, for example, of the surrounding medium. By way of example, the spacer portion 106 may swell (e.g., retain water) or shrink (e.g., expel of water) in response to pH. In addition, the spacer portion 106 may also be characterized as rheoreversible in which the hydrogel gel may be formed by reaction of a suitable polymer material with carbon dioxide. This procedure may be reversible, for example, by carbon dioxide depressurization or by solubilizing with a diluted acid. Without limitation, rheoreversible hydrogels may be obtained using polyamines, such as polyallylamine and polyethyleneimine. This response may result in changing the configuration of the magnetic complex 100 and, thus the spacing of the first magnetic portion 102 and the second magnetic portion 104. By changing the spacing, the electromagnetic response to an external field also changes. Accordingly, by measuring the frequency response, the shape of the magnetic complex 100 may be determined. Use of a range of frequencies for the external electromagnetic field 110 may facilitate this determination.

Figure 2:
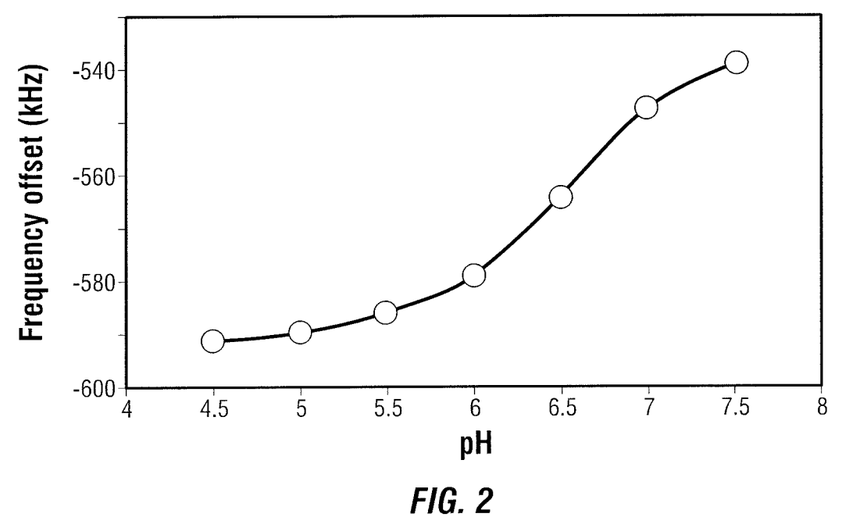
FIG. 2 is a chart showing change in resonance frequency as a function of fluid pH values for an example magnetic complex.

FIG. 2 is a chart illustrating the example response of a magnetic complex 100 in response to pH. The left side of the chart illustrates the magnetic complex in a surrounding medium that is acidic. As the pH increases, from left to right (e.g., from acidic to basic), there may be a resultant swelling of the spacer portion 106 with a change in spacing between the first magnetic portion 102 and the second magnetic portion 104. With this change, there is a resultant change in resonance frequency of the spacer portion 106, indicated on FIG. 2 as frequency offset in kilohertz.

The spacer portion 106 may also be responsive to additional stimuli in place or in combination with pH. Without limitation, the spacer portion 106 may be responsive to one or more of temperature, electric field, magnetic field, pressure, sound, ionic strength, or chemical species, among others. For example, the spacer portion 106 may be selected so that it is thermoresponsive in that the spacer portion 106 may swell or shrink in response to temperature changes. By way of further example, the spacer portion 106 may be electrically modulated in that the spacer portion 106 may swell or shrink in response to magnetic or electric field strength. This swelling or shrinking may cause a change in magnetic flux density with a resultant change in frequency response. Without limitation, for a spacer portion 106 that is thermoresponsive or electrically modulated, the spacer portion 106 may comprise a polymer composite. Non-limiting examples of polymer composites may include polymer gels (e.g., hydrogels), copolymers, porous membranes, liquid crystalline polymeric membranes, or combinations thereof. One of ordinary skill in the art, with the benefit of this disclosure, should be able to select an appropriate polymer spacer 106 and stimuli response as a desired for a particular application.

The spacer portion 106, for example, may be functionalized such that the functionalized polymeric material may be chemically sensitive. Accordingly, the spacer portion 106 may swell or shrink in response to chemical species in the surrounding medium. By having sensitivity to specific fluids or chemicals downhole, the magnetic complex 100 may be used as a chemical sensor downhole. In this manner, the magnetic complex 100 may be used to detect specific fluids, such as an oil, water, short-chain hydrocarbons, natural gas, $C_2O$, $H_2S$, or combinations thereof, among others. The frequency response of the magnetic complex 100 for example, may be used to detect the chemical species in the surrounding medium.

The magnetic complex 100 may have a size selected based on a number of factors, including the specific application. Without limitation, the magnetic complex 100 may be very small so that they may be pumpable in a carrier fluid for placement downhole. The size of the magnetic complex 100 may be selected depending on a number of factors, including its particular application. The magnetic complex 100 may have a size that ranges from nano-scale (e.g., a few nanometers) to several hundreds of microns or millimeters in size.

As previously described, the magnetic complex 100 (or a plurality of magnetic complexes 100) may be placed downhole for use in wellbore monitoring. For placement downhole, a plurality of magnetic complexes 100 may be included in a carrier fluid. Any of a variety of suitable carrier fluids may be used, including oil-based or aqueous-based fluids. Without limitation, the carrier fluid may be a wellbore treatment fluid, such as a fracturing fluid, cement composition, spacer fluid, completion fluid, or injection fluid, among others.

Figure 3:
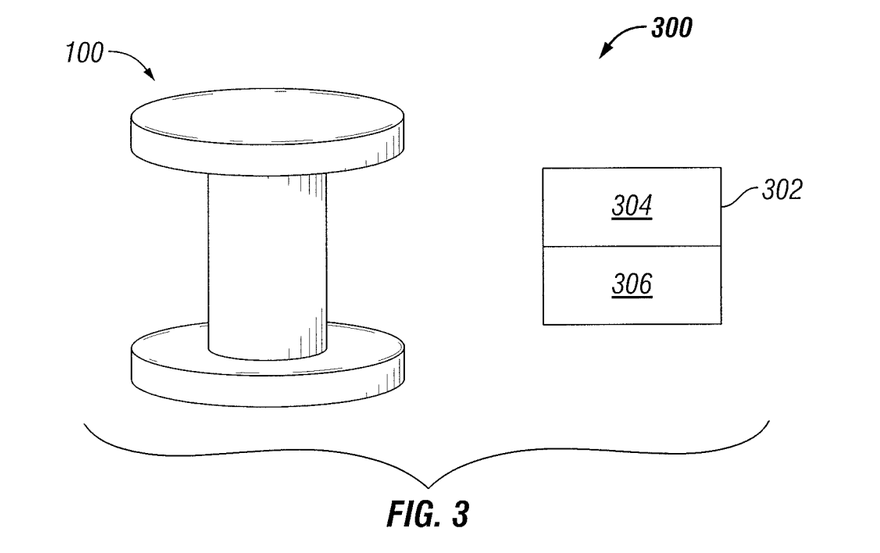
FIG. 3 is a schematic illustration of a wellbore monitoring system.

FIG. 3 illustrates a wellbore monitoring system 300 that comprises a magnetic complex 100. As illustrated, the wellbore monitoring system 300 may comprise the magnetic complex 100 and an electromagnetic interrogator 302. The electromagnetic interrogator 302 may comprise an electromagnetic energy source 304 and an electromagnetic detector 306. The electromagnetic energy source 304 may be operable to generate external electromagnetic field 110. The external electromagnetic field 110 may be a radiofrequency field, wherein the electromagnetic energy source 304 may be considered a radiofrequency transmitter. Without limitation, the electromagnetic energy source 304 may generate a range of frequencies that may be used to excite the magnetic complex 100. The electromagnetic detector 306 may be operable to detect electromagnetic waves originating from the magnetic complex 100 after the magnetic complex 100 is excited with the external electromagnetic field 110 from the electromagnetic energy source 304. While not shown, the electromagnetic interrogator 302 may further comprise a processor, a memory component, a communications component, or both. The memory component may store raw and/or processed data detected by the electromagnetic detector 306. The communications may transmit raw data to the processor and/or transmit processed data to another receiver, for example, located at the surface. The communications component may communicate via wired or wireless communications.

The components (e.g., electromagnetic energy source 304, electromagnetic detector 306, processor, memory component, and/or communications component) may be coupled together and in signal communication with one another. One or more of the components of the electromagnetic interrogator 302 may be integrated into a tool or unit that is temporarily or permanently placed downhole. The electromagnetic interrogator 302 may be installed in the wellbore, for example, coupled to a downhole component, such as a casing, casing attachment, plug, tubing string, or the like. Alternatively, the electromagnetic interrogator 302 may be run into the wellbore, for example, on a wireline. In some instances, more than one electromagnetic interrogator 302 may be used. Without limitation, the electromagnetic interrogator 302 may be installed at different depths in the wellbore, for example to provide different spacing for the electromagnetic energy source 304 and electromagnetic detector 306. Different spacing may allow for different depths of investigation, which may make it possible to have azimuthal sensitivity.

Figure 4:
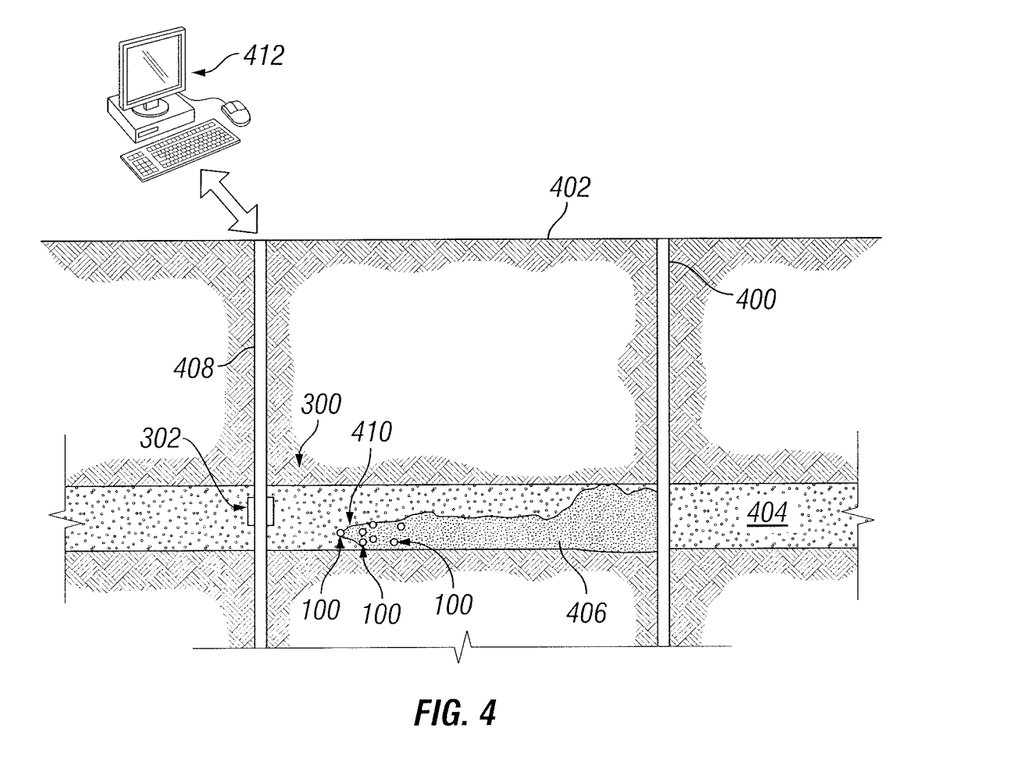
FIG. 4 is a schematic illustration showing an example use of magnetic complexes in a water flood operation.

FIG. 4 is a schematic illustration showing use of wellbore monitoring system 300 in a waterflood monitoring operation. As illustrated, an injection well 400 may be drilled from surface 402 into subterranean formation 404. Injection well 400 may be used to inject a treatment fluid 406 into the subterranean formation 404. Any suitable treatment fluid for use in waterflood monitoring operations may be used, including, for example, aqueous-based treatment fluids. The treatment fluid 406 may be forced through subterranean formation 404 to production well 408. The treatment fluid may, in turn, force reservoir fluid (e.g., oil or other desirable fluids) contained in subterranean formation 404 to production well 408. The reservoir fluid may then be directed to surface 402 by way of production well 408. In waterflood monitoring operations, it may be desirable to monitor progress of treatment fluid 406 from injection well 400 to production well 408. The interface between the reservoir fluid and the injected fluid, illustrated on FIG. 4 as flood front 410, may develop protrusions and irregularities that may reach production well 408 before a desired amount of the reservoir fluid has been flushed from subterranean formation 404. Without limitation, this breakthrough of the treatment fluid 406 may be undesirable, for example, by increasing fluid handling requirements by dilution of reservoir fluid with treatment fluid 406.

Wellbore monitoring system 300 may be used in the waterflood monitoring operation to monitor progress of treatment fluid 406 from injection well 400 to production well 408. By use of wellbore monitoring system 300, the flood front 410 may be monitored, for example, so that corrective actions may be taken to optimize production of reservoir fluid from subterranean formation 404. Wellbore monitoring system 300 may include magnetic complex 100, electromagnetic interrogator 302, and processing system 412. As illustrated, a magnetic complex 100 (or plurality of magnetic complexes 100) may be placed into subterranean formation 404, for example, by way of injection well 400. Without limitation, magnetic complexes 100 may be carried in treatment fluid 406 that may be injected into subterranean formation 404. Electromagnetic interrogator 302 may be used to energize magnetic complexes 100 and detect electromagnetic waves emitted from magnetic complexes 100. As illustrated, electromagnetic interrogator 302 may be installed in production well 408, for example, coupled to a downhole component, such as a casing, casing attachment, plug, tubing string, or the like. Alternatively, electromagnetic interrogator 302 may be run into production well 408 on a wireline. The detected electromagnetic waves from magnetic complexes 100 may be used to track flood front

410. The magnetic complexes 100 may be desired for azimuthal sensitivity. Without limitation, the magnetic complexes 100 may comprise two or more groups of magnetic complexes 100 that have different resonance frequencies, thus enabling monitoring more than one flood channel. Without limitation, the placement of the magnetic complexes 100 with different resonance frequencies in the injection well 400 may also be controlled.

As illustrated, wellbore monitoring system 300 may further comprise a processing system 412. Processing system 412 may be coupled to electromagnetic interrogator 302 by communication link 414, which may be a wired or wireless connection. The processing system 412, which may be computer or other suitable microprocessor, for example, may act as a data acquisition system and possibly a data processing system that analyzes the measurements, for example, to track location of flood front 410. The processing system 412 may further control production parameters, for example, to reduce risk of break through or otherwise to optimize production based on information derived from the measurements. In response to the information derived from the measurements, one or more production and/or injection parameters may be changed. Production parameters may include the flow rate/pressure permitted from selected production zones and injection parameters flow rate/pressure in selected injection zones, and the composition of the injection fluid, each of which can be controlled via computer controlled valves and pumps, for example. While processing system 412 is shown at surface 402, the present technique is intended to encompass use of processing system 412 downhole.

Figure 5:
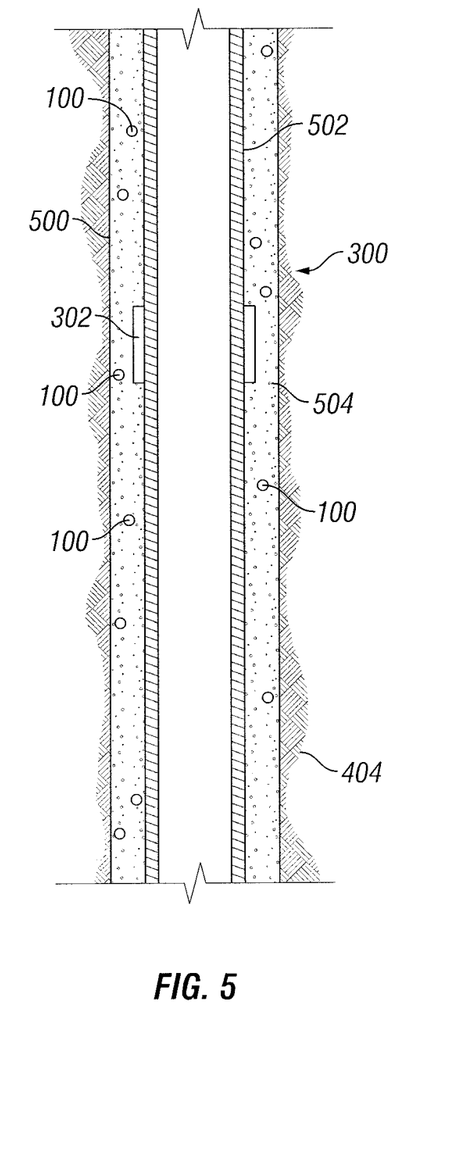
FIG. 5 is a schematic illustration showing an example use of magnetic complexes in a cementing operation.

FIG. 5 is a schematic illustration showing use of wellbore monitoring system 300 in a cementing operation. As illustrated, a wellbore 500 may be drilled into subterranean formation 404. At a desired time, a wellbore conduit 502 (e.g., casing, pipe string, liner, etc.) may be run into wellbore 500 and cemented in place. The process of cementing the wellbore conduit 502 in place is commonly referred to as "primary cementing." In a typical primary cementing method, a cement composition 504 may be pumped into an annulus between the walls of the well bore 500 and the exterior surface of the wellbore conduit 502 disposed therein (or between wellbore conduit 502 and a larger conduit). Other techniques may also be utilized for introduction of the cement composition 504. By way of example, reverse circulation techniques may be used that include introducing the cement composition 504 by way of the annulus instead of through the wellbore conduit 502. The cement composition 504 may set in the annular space, thereby forming an annular sheath of hardened, substantially impermeable cement (i.e., a cement sheath) that may support and position the wellbore conduit 502 in the well bore 500 and may bond the exterior surface of the wellbore conduit 502 to the subterranean formation 404. In wellbore cementing, it may be desirable to monitor cement hydration as other wellbore operations may be suspended until the cement composition 504 has set.

Wellbore monitoring system 300 may be used in the cementing operation to monitor hydration of cement composition 504. By use of wellbore monitoring system 300, cement hydration may be monitored to detect when the cement composition 504 has set (e.g., sufficient hardening of the cement sheath) thus reducing wait-on-cement time and potentially enabling quicker resumption of other wellbore operations, such as drilling and completion operations. Wellbore monitoring system 300 may include magnetic complex 100 and electromagnetic interrogator 302. While not shown on FIG. 5, wellbore monitoring system 300 may further include processing system 412 (e.g., FIG. 4). As illustrated, a magnetic complex 100 (or plurality of magnetic complexes 100) may be included in cement composition 504. As previously described, the magnetic complexes 100 may respond to pH. As cement composition 504 hydrates, the pH will change as will the water content. Accordingly, the shape of the magnetic complexes 100 may change as cement composition 504 hydrates in wellbore 500. At the end of the process, with no water available, and the cement composition 504 set, the shape of the magnetic complex 100 and, thus the detected resonance frequency will no longer change. During hydration, electromagnetic interrogator 302 may be used to energize magnetic complexes 100 and detect electromagnetic waves emitted, reflected, transmitted, or absorbed from magnetic complexes 100. As illustrated, electromagnetic interrogator 302 may be installed in wellbore 500, for example, coupled to wellbore conduit 502 (or other downhole component). Alternatively, electromagnetic interrogator 302 may be run into wellbore 500 on a wireline. The detected electromagnetic waves from magnetic complexes 100 may be used to track hydration of cement composition 504. The processing system 412 (e.g., FIG. 4) may act as a data acquisition system and possibly a data processing system that analyzes the measurements, for example, to track hydration of the cement composition 504. In response to information derived from the measurements, wellbore operations may be resumed.

Figure 6:
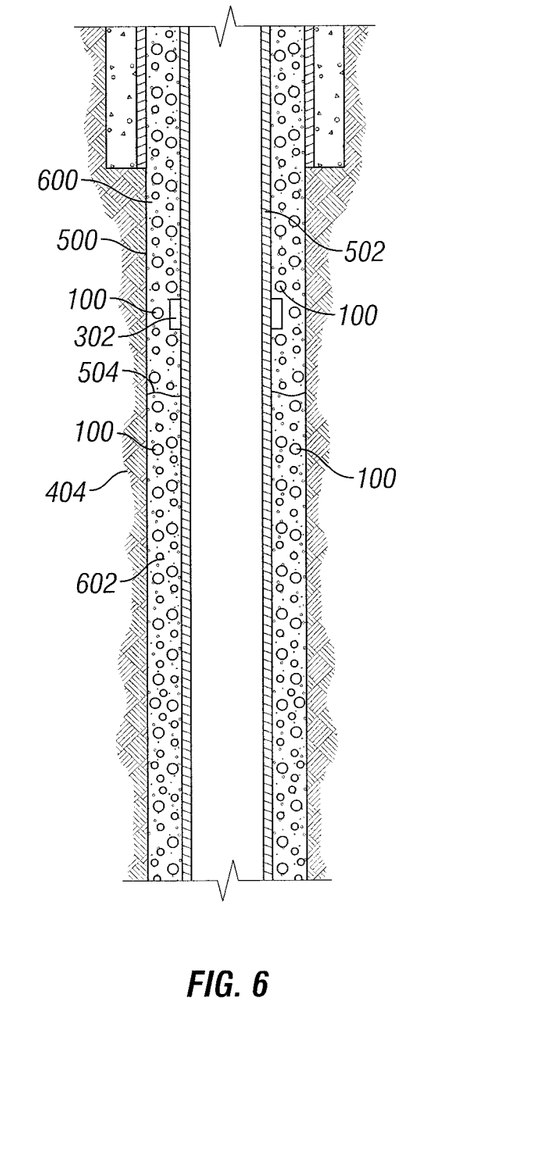
FIG. 6 is a schematic illustration showing an example use of magnetic complexes for determining fluid interfaces in well operations.

FIG. 6 is a schematic illustration showing use of wellbore monitoring system 300 in determining a fluid interface. As illustrated, wellbore 500 may be drilled into subterranean formation 404. Wellbore conduit 502 (e.g., casing, pipe string, liner, etc.) may be run into wellbore 500. As illustrated, a first fluid 600 and a second fluid 602 may be introduced into an annulus between the walls of the well bore 500 and the exterior surface of the wellbore conduit 502 disposed therein (or between wellbore conduit 502 and a larger conduit). First fluid 600 may be a drilling fluid, spacer fluid, cement composition, or other suitable treatment fluid. Second fluid 602 may be a drilling fluid, spacer fluid, cement composition, or other suitable fluid. It may be desirable to determine a fluid interface 604 between first fluid 600 and second fluid 602. For example, where second fluid 602 is a cement composition, it may be desirable to determine the top of the cement composition, often referred to as top of cement. Without limitation, this may be beneficial to determine if the cement composition, for example covers the desired zone.

Wellbore monitoring system 300 may be used to monitor first fluid 600 and second fluid 602, for example, to determine fluid interface 604. Wellbore monitoring system 300 may include magnetic complex 100 and electromagnetic interrogator 302. While not shown on FIG. 6, wellbore monitoring system 300 may further include processing system 412 (e.g., FIG. 4). As illustrated, a magnetic complex 100 (or plurality of magnetic complexes 100) may be included in first fluid 600 and/or second fluid 602. Without limitation, magnetic complexes 100 may be disposed in first fluid 600, second fluid 602, or both first fluid 600 and second fluid. As previously described, the magnetic complexes 100 may be responsive to a number of stimuli including pH, hydration, water content, and chemistry, among others. Accordingly, the magnetic complexes 100 in first fluid 600 may respond differently than the magnetic complexes in second fluid 602, thus providing different separation between first magnetic portion 102 and second magnetic portion 104 (e.g., FIG. 1) in each fluid, which in turn provides different frequency responses. For fluids that may be low in water content, the spacer portion 106 may include a polymer mesh or other suitable material, instead of hydrogels, that can respond to oil-based fluids. Electromagnetic interrogator 302 may be used to energize magnetic complexes 100 and detect electromagnetic waves emitted, reflected, transmitted, or absorbed from magnetic complexes 100. As illustrated, electromagnetic interrogator 302 may be installed in wellbore 500, for example, coupled to wellbore conduit 502 (or other downhole component). Alternatively, electromagnetic interrogator 302 may be run into wellbore 500 on a wireline. The detected electromagnetic waves from magnetic complexes 100 may be used to track hydration of cement composition 504. The processing system 412 (e.g., FIG. 4) may act as a data acquisition system and possibly a data processing system that analyzes the measurements, for example, to determine fluid interface 604.

Figure 7:
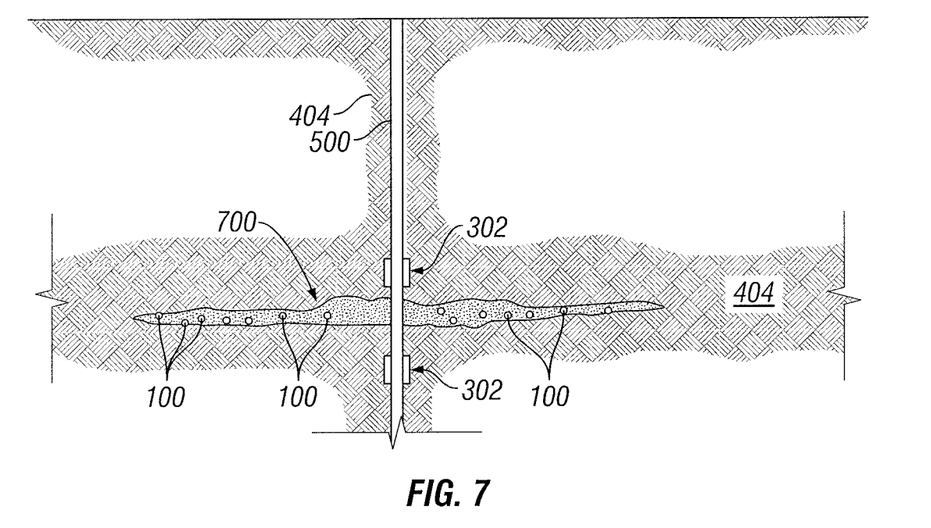
FIG. 7 is a schematic illustration showing an example use of magnetic complexes for fracture mapping in well operations.

FIG. 7 is a schematic illustration showing use of wellbore monitoring system 300 in determining a fracturing operation. As illustrated, wellbore 500 may be drilled into subterranean formation 404. At a desired time, one or more fractures 700 may be created or enhanced in subterranean formation 404. Fractures 700 may extend from wellbore 500 into subterranean formation 404. Fractures 700 may increase flow of reservoir fluids into wellbore 500 from subterranean formation 404. It may be desirable to have an understanding of fracture geometry. Without limitation, having an understanding of fracture geometry may be used, for example, in determining well spacing and field development strategies.

Figure 8:
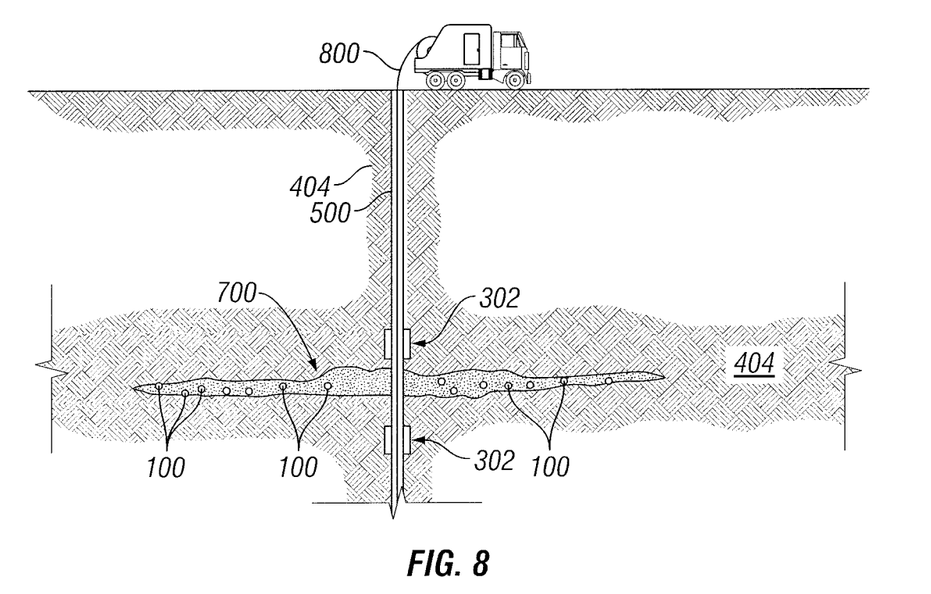
FIG. 8 is a schematic illustration showing an example use of magnetic complexes for fracture mapping in well operations.

Wellbore monitoring system 300 may be used to monitor fractures 700, for example, to model fracture geometry. Wellbore monitoring system 300 may include magnetic complex 100 and electromagnetic interrogator 302. While not shown in FIG. 7, wellbore monitoring system 300 may further include processing system 412 (e.g., FIG. 4). As illustrated, a magnetic complex 100 (or plurality of magnetic complexes 100) may be included introduced into fractures 700. Without limitation, magnetic complexes 100 may be included in a fracturing fluid injected into subterranean formation 404 and deposited into fractures 700. Electromagnetic interrogator 302 may be used to energize magnetic complexes 100 and detect electromagnetic waves emitted, reflected, transmitted, or absorbed from magnetic complexes 100. As illustrated, electromagnetic interrogator 302 may be installed in wellbore 500, for example, coupled to tubing or other wellbore conduit (e.g., FIG. 6) in wellbore 500. Alternatively, electromagnetic interrogator 302 may be run into wellbore 500 on wireline 800, as shown in FIG. 8. The detected electromagnetic waves from magnetic complexes 100 may be used to monitor fractures 700, for example, to model fracture geometry. Without limitation, the extent and dimensions of fractures 700 may be determined. This provides information about the location of the fracturing fluid. Magnetic complexes 100 may be used to monitor fractures 700 during and/or after a fracturing operation. The processing system 412 (e.g., FIG. 4) may act as a data acquisition system and possibly a data processing system that analyzes the measurements, for example, to determine a model of fracture geometry. As illustrated on FIG. 7, multiple electromagnetic interrogators 302 may be disposed in wellbore 500, for example, to provide different source-detector spacing. The electromagnetic interrogators 302 may also be placed in different quadrants around wellbore 500. Different source-detector spacing may enable different depths of investigation. The multi-quadrant configuration may enable azimuthal sensitivity. By combing different source-detector spacing and multi-quadrant configurations, measurements may be used to determine both dimension and orientation of fractures 700.

Figure 9:
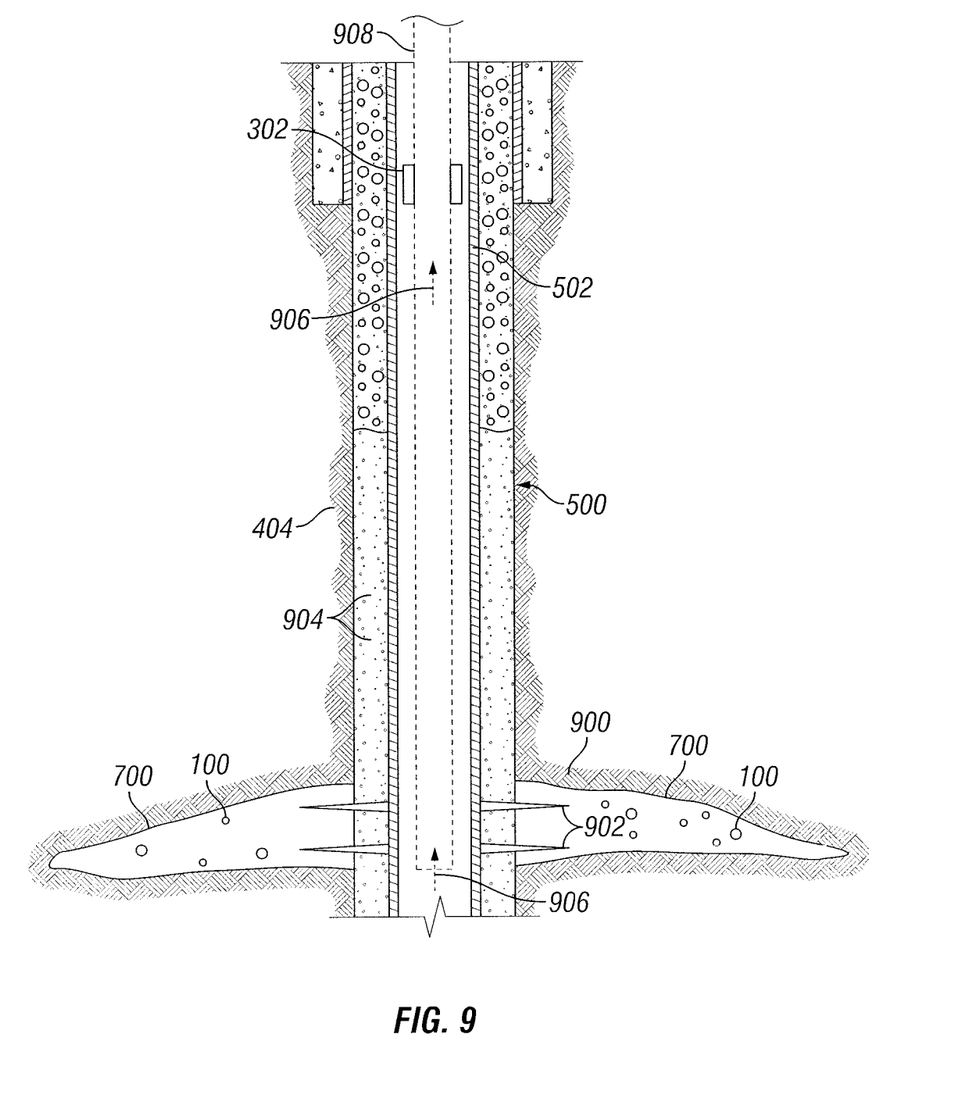
FIG. 9 is a schematic illustration showing an example use of magnetic complexes for production monitoring.

FIG. 9 is a schematic illustration showing use of wellbore monitoring system 300 in production monitoring. As illustrated, wellbore 500 may be drilled into subterranean formation 404, which may contain production zone 900. Wellbore conduit 502 may be disposed in wellbore 500. Perforations 902 may provide communication between production zone 900 and wellbore 500. As illustrated, perforations 902 may extend through wellbore conduit 502 and cement sheath 904. Reservoir fluids 906 may flow from production zone 900 and through perforations 902 into wellbore 500. Reservoir fluids 906 may be conveyed to surface 402 (e.g., FIG. 4) by way of production tubing 908, which may be disposed in wellbore conduit 502. It may be desirable to monitor production of reservoir fluids.

Wellbore monitoring system 300 may be used to monitor production of reservoir fluid. Wellbore monitoring system 300 may include magnetic complex 100 and electromagnetic interrogator 302. While not shown in FIG. 9, wellbore monitoring system 300 may further include processing system 412 (e.g., FIG. 4). As illustrated, a magnetic complex 100 (or plurality of magnetic complexes 100) may be disposed in production zone 900. Without limitation, magnetic complexes 100 may be disposed in fractures 700 in production zone 900. Without limitation, magnetic complexes 100 may be included in a fracturing fluid injected into subterranean formation 404 and deposited into fractures 700. As reservoir fluid is produced, magnetic complexes 100 may travel with reservoir fluid from production zone and up through production tubing 908, for example Electromagnetic interrogator 302 may be used to energize magnetic complexes 100 and detect electromagnetic waves emitted, reflected, transmitted, or absorbed from magnetic complexes 100. As illustrated, electromagnetic interrogator 302 may be installed in wellbore 500, for example, coupled to production tubing 908 or another wellbore conduit (e.g., FIG. 6) in wellbore 500. Alternatively, electromagnetic interrogator 302 may be installed at the surface. The detected electromagnetic waves from magnetic complexes 100 may be used to monitor fractures 700, for example, to model fracture geometry. Without limitation, the extent and dimensions of fractures 700 may be determined. Magnetic complexes 100 may be used to monitor production of reservoir fluid. Without limitation, magnetic complexes 100 that have different resonance frequencies may be disposed at different locations in subterranean formation 404, for example, to monitor location of production, for example, where there are multiple production zones 900. The processing system 412 (e.g., FIG. 4) may act as a data acquisition system and possibly a data processing system that analyzes the measurements, for example, to monitor production.

Accordingly, the present disclosure provide for methods and systems that use magnetic complexes in well monitoring. Without limitation, the systems and methods of the present disclosure may include one or more of the following statements:

Statement 1: A well monitoring system comprising: magnetic complexes disposed in a subterranean formation, wherein the magnetic complexes each comprise a first magnetic portion, a second magnetic portion, and a spacer portion; and an electromagnetic interrogator, wherein the electromagnetic interrogator comprises an electromagnetic source and an electromagnetic detector.

Statement 2: The system of statement 1, wherein the first magnetic portion and the second magnetic portion are each disc shaped, and wherein the spacer portion comprises a hydrogel.

Statement 3: The system of statement 1 or 2, wherein the spacer portion comprises at least one hydrogel selected from the group consisting of polyacrylamide, hydrolyzed polyacrylamide, copolymers of acrylamide with ethylenically unsaturated ionic comonomers, copolymers of acrylamide and acrylic acid salts, poly(acrylic acid) or salts thereof, polyethyleneglycol, polyvinylpyrrolidone, polyvinylalcohol, carboxymethyl cellulose, hydroxyethyl cellulose, hydroxypropyl cellulose, guar gum, carboxymethyl guar, carboxymethyl hydroxypropyl guar gum, hydrophobically associating swellable emulsion polymers, and latex polymers.

Statement 4: The system of any one of statements 1 to 3, wherein the spacer portion is responsive to at least one stimuli to cause the spacer portion to change shape, wherein the at least one stimuli is selected from the group consisting of pH, temperature, electric field, magnetic field, pressure, sound, ionic strength, and chemical species.

Statement 5: The system of any one of statements 1 to 4, wherein the spacer portion comprises at least one material selected from the group consisting of a hydrogel, a water-swellable clay, a water-swellable elastomer, a thermoplastic-elastomer composite, and combinations thereof.

Statement 6: The system of any one of statements 1 to 5, wherein the spacer portion comprises nanoparticles.

Statement 7: The system of any one of statements 1 to 6, wherein the electromagnetic interrogator is coupled to a wellbore conduit or disposed on a wireline.

Statement 8: The system of any one of statements 1 to 7, wherein the magnetic complexes are disposed in a fracture in the subterranean formation.

Statement 9: The system of any one of statements 1 to 8, wherein the magnetic complexes are present in a treatment fluid injected into the subterranean formation by way of an injection well, wherein the electromagnetic interrogator is disposed in a production well.

Statement 10: The system of any one of statements 1 to 9, wherein the magnetic complexes are present in a reservoir fluid produced through a wellbore.

Statement 11: The system of any one of statements 1 to 7, wherein the magnetic complexes are present in a first fluid disposed in a wellbore annulus adjacent to a second fluid disposed in the wellbore annulus.

Statement 12: The system of any one of statements 1 to 7, wherein the magnetic complexes are disposed in a cement composition disposed in a wellbore annulus.

Statement 13: The system of any one of statements 1 to 12, further comprising a plurality of electromagnetic interrogators positioned in a wellbore, wherein the electromagnetic interrogators each comprise an electromagnetic source and an electromagnetic detector.

Statement 14: A method of wellbore monitoring comprising: introducing magnetic complexes into a subterranean formation, wherein the magnetic complexes each comprise a first magnetic portion, a second magnetic portion, and a spacer portion; applying an external electromagnetic field to the magnetic complexes; and measuring a frequency response of the magnetic complexes to the magnetic field.

Statement 15: The method of statement 14, wherein an external stimulus changes a shape of the polymeric space and, in turn, the geometry between the first magnetic portion and the second magnetic portion.

Statement 16: The method of statement 14 or 15, wherein the introducing the magnetic complexes into the subterranean formation comprises depositing the magnetic complexes into one or more fractures in the subterranean formation, wherein the frequency response is used to map fracture geometry.

Statement 17: The method of any one of statements 14 to 16, wherein the introducing the magnetic complexes into the subterranean formation comprises introducing the magnetic complexes through an injection well, wherein the measuring occurs while the magnetic complexes migrate from the injection well toward a production well to determine a flood front.

Statement 18: The method of any one of statements 14 to 16, wherein the introducing the magnetic complexes into the subterranean formation comprises introducing the magnetic complexes into a wellbore annulus, wherein the magnetic complexes are disposed in a cement composition, and wherein the measuring occurs while the cement composition hydrates to monitor cement hydration.

Statement 19: The method of any one of statements 14 to 16, wherein the introducing the magnetic complexes into the subterranean formation comprises introducing a first fluid comprising a first portion of magnetic complexes into a wellbore annulus and introducing a second fluid comprising a second portion of magnetic complexes into the wellbore annulus, and further comprising analyzing the frequency responses to determine a fluid interface between the first fluid and the second fluid.

Statement 20: The method of any one of statements 14 to 16, wherein at least a portion of the magnetic complexes are produced from a wellbore in a reservoir fluid, and wherein the measuring occurs while the magnetic complexes are produced.

Statement 21: The method of any one of statements 14 to 20, wherein the magnetic features include one or more of the features define by any one statements 2-6.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A well monitoring system comprising:
   magnetic complexes disposed in a subterranean formation, wherein the magnetic complexes each comprise a first magnetic portion, a second magnetic portion, and a spacer portion; and
   an electromagnetic interrogator, wherein the electromagnetic interrogator comprises an electromagnetic source and an electromagnetic detector; and
   a processor in communication with the electromagnetic interrogator, the processor operable to control a flow rate in the subterranean formation based on frequency responses of the magnetic complexes.

2. The system of claim 1, wherein the first magnetic portion and the second magnetic portion are each disc shaped, and wherein the spacer portion comprises a hydrogel.

3. The system of claim 1, wherein the spacer portion comprises at least one hydrogel selected from the group consisting of polyacrylamide, hydrolyzed polyacrylamide, copolymers of acrylamide with ethylenically unsaturated ionic comonomers, copolymers of acrylamide and acrylic acid salts, poly(acrylic acid) or salts thereof, polyethyleneglycol, polyvinylpyrrolidone, polyvinylalcohol, carboxymethyl cellulose, hydroxyethyl cellulose, hydroxypropyl cellulose, guar gum, carboxymethyl guar, carboxymethyl hydroxypropyl guar gum, hydrophobically associating swellable emulsion polymers, and latex polymers.

4. The system of claim 1, wherein the spacer portion is responsive to at least one stimuli to cause the spacer portion to change shape, wherein the at least one stimuli is selected from the group consisting of pH, temperature, electric field, magnetic field, pressure, sound, ionic strength, and chemical species.

5. The system of claim 1, wherein the spacer portion comprises at least one material selected from the group consisting of a hydrogel, a water-swellable clay, a water-swellable elastomer, a thermoplastic-elastomer composite, and combinations thereof.

6. The system of claim 1, wherein the spacer portion comprises nanoparticles.

7. The system of claim 1, wherein the electromagnetic interrogator is coupled to a wellbore conduit or disposed on a wireline.

8. The system of claim 1, wherein the magnetic complexes are disposed in a fracture in the subterranean formation.

9. The system of claim 1, wherein the magnetic complexes are present in a treatment fluid injected into the subterranean formation by way of an injection well, wherein the electromagnetic interrogator is disposed in a production well.

10. The system of claim 1, wherein the magnetic complexes are present in a reservoir fluid produced through a wellbore.

11. The system of claim 1, wherein the magnetic complexes are present in a first fluid disposed in a wellbore annulus adjacent to a second fluid disposed in the wellbore annulus.

12. The system of claim 1, wherein the magnetic complexes are disposed in a cement composition disposed in a wellbore annulus.

13. The system of claim 1, further comprising a plurality of electromagnetic interrogators positioned in a wellbore, wherein the electromagnetic interrogators each comprise an electromagnetic source and an electromagnetic detector.

14. A method of wellbore monitoring comprising:
    introducing magnetic complexes into a subterranean formation, wherein the magnetic complexes each comprise a first magnetic portion, a second magnetic portion, and a spacer portion;
    applying an external electromagnetic field to the magnetic complexes; measuring frequency responses of the magnetic complexes to a magnetic field; and
    controlling a flow rate in the subterranean formation based on the frequency responses of the magnetic complexes.

15. The method of claim 14, further comprising determining geometry, hydration state, chemical composition, temperature, and local field strength based on the magnetic complexes.

16. The method of claim 14, wherein the introducing the magnetic complexes into the subterranean formation comprises depositing the magnetic complexes into one or more fractures in the subterranean formation, wherein the frequency response is used to map fracture geometry.

17. The method of claim 14, wherein the introducing the magnetic complexes into the subterranean formation comprises introducing the magnetic complexes through an injection well, wherein the measuring occurs while the magnetic complexes migrate from the injection well toward a production well to determine a flood front.

18. The method of claim 14, wherein the introducing the magnetic complexes into the subterranean formation comprises introducing the magnetic complexes into a wellbore annulus, wherein the magnetic complexes are disposed in a cement composition, and wherein the measuring occurs while the cement composition hydrates to monitor cement hydration.

19. The method of claim 14, wherein the introducing the magnetic complexes into the subterranean formation comprises introducing a first fluid comprising a first portion of magnetic complexes into a wellbore annulus and introducing a second fluid comprising a second portion of magnetic complexes into the wellbore annulus, and further comprising analyzing the frequency responses to determine a fluid interface between the first fluid and the second fluid.

20. The method of claim 14, wherein at least a portion of the magnetic complexes are produced from a wellbore in a reservoir fluid, and wherein the measuring occurs while the magnetic complexes are produced.

* * * * *